(12) United States Patent
Krattiger et al.

(10) Patent No.: US 8,810,639 B2
(45) Date of Patent: Aug. 19, 2014

(54) ENDOSCOPIC VIDEO MEASURING SYSTEM (75) Inventors: Beat Krattiger, Beringen (CH); Martin Klumpp, Radolfzell-Markelfingen (DE); Manfred Kuster, Schaffhausen (CH)

(73) Assignee: Storz Endoskop Produktions GmbH (DE)

( * ) Notice: Subject to any disclaimer, the term of this patent is extended or adjusted under 35 U.S.C. 154(b) by 1711 days.

(21) Appl. No.: 11/676,016

(22) Filed: Feb. 16, 2007

(65) Prior Publication Data

US 2007/0139953 A1   Jun. 21, 2007

Related U.S. Application Data (63) Continuation of application No. PCT/EP2005/008663, filed on Aug. 10, 2005.

(30) Foreign Application Priority Data

Aug. 19, 2004   (DE) .................... 20 2004 012 992 U (51) Int. Cl.
*A61B 1/04* (2006.01)
*A61B 1/06* (2006.01)

(52) U.S. Cl.
USPC ................ 348/68; 348/65; 362/574; 600/175

(58) Field of Classification Search
USPC .................. 348/68, 65; 362/574; 600/175
See application file for complete search history.

(56) References Cited

U.S. PATENT DOCUMENTS

| | | | |
|---|---|---|---|
| 3,595,220 A | 7/1971 | Kawahara | 128/6 |
| 3,817,631 A * | 6/1974 | Kawahara | 356/3.11 |
| 4,569,334 A * | 2/1986 | Ohshiro | 600/182 |
| 4,660,982 A | 4/1987 | Okada | 356/383 |
| 4,706,653 A | 11/1987 | Yamamoto | 128/4 |
| 4,856,495 A | 8/1989 | Tohjoh et al. | 128/6 |
| 5,014,709 A * | 5/1991 | Bjelkhagen et al. | 600/431 |
| 5,045,936 A | 9/1991 | Lobb et al. | 358/100 |
| 5,436,655 A * | 7/1995 | Hiyama et al. | 348/45 |
| 5,512,036 A | 4/1996 | Tamburrino et al. | 600/172 |
| 5,609,561 A | 3/1997 | Uehara et al. | 600/112 |

(Continued)

FOREIGN PATENT DOCUMENTS

DE   35 16 164 C2   11/1985
DE   103 08 383 A1   9/2004

OTHER PUBLICATIONS

German Search Report, Apr. 19, 2005, 2 pages.
International Search Report, Nov. 4, 2005, 3 Pages.

(Continued)

*Primary Examiner* — Viet Vu
*Assistant Examiner* — Herman Belcher
(74) *Attorney, Agent, or Firm* — St. Onge Steward Johnston & Reens LLC (57) ABSTRACT

An endoscopic video measurement system having a proximal operating part, an insertion part, and a replaceable head that can be inserted thereon, and where the operating part contains a connection for supplying electrical and optical power, optical transmission means for the lens illumination are provided in the insertion part for an electronic image sensor positioned in the distal end portion, and the replaceable head contains optical transmission means for the lens illumination and lens imaging, is characterized in that, in the insertion part, for transmitting a measurement beam a single-mode optical fiber is provided, with which an optical system positioned in the distal end part of the insertion part for producing a collimated sample beam bundle is associated.

7 Claims, 4 Drawing Sheets

(56) References Cited

U.S. PATENT DOCUMENTS

| | | | |
|---|---|---|---|
| 5,669,871 A | 9/1997 | Sakiyama | 600/117 |
| 5,711,756 A | 1/1998 | Chikama | 600/112 |
| 6,071,233 A * | 6/2000 | Ishikawa et al. | 600/104 |
| 6,135,947 A | 10/2000 | Watanabe et al. | 600/178 |
| 6,184,923 B1 | 2/2001 | Miyazaki | 348/75 |
| 6,361,491 B1 * | 3/2002 | Hasegawa et al. | 600/175 |
| 6,482,148 B1 | 11/2002 | Luke | 600/117 |
| 7,259,847 B2 * | 8/2007 | Rigler et al. | 356/318 |
| 2004/0143162 A1 * | 7/2004 | Krattiger et al. | 600/175 |
| 2005/0013328 A1 * | 1/2005 | Jurgensen | 372/6 |

OTHER PUBLICATIONS

Translation of the International Report on Patentability, Apr. 12, 2007, 5 pages.

* cited by examiner

ENDOSCOPIC VIDEO MEASURING SYSTEM

CROSS-REFERENCE TO RELATED APPLICATIONS

The present application is a continuation of pending International patent application PCT/EP2005/008663 filed on Aug. 10, 2005 which designates the United States and claims priority from German patent application 20 2004 012 992.2 filed on Aug. 19, 2004, the content of which is incorporated herein by reference.

FIELD OF THE INVENTION

The invention relates to an endoscopic video measurement system having a proximal operating part, an insertion part, and a replaceable head that can be inserted thereon, and where the operating part contains a connection for supplying electrical and optical power, optical transmission means for the lens illumination are provided in the insertion part for an electronic image sensor positioned in the distal end portion, and the replaceable head contains optical transmission means for the lens illumination and lens imaging.

BACKGROUND OF THE INVENTION

Endoscopy is an auxiliary means for inspecting concealed hollow cavities. Their fields of application, in addition to medicine, are found in technology, for instance in loss analysis or quality control.

Endoscopy is experiencing growing popularity in technology because the available working diameters are becoming progressively smaller. The image quality is constantly improving through improved light sources, lenses, and materials. In addition, the increase in miniaturized components in video technology helped endoscopy achieve expanding publicity.

With the growing spread of video endoscopy, there has also been a rise in the need for geometrically measuring and manipulating in concealed hollow cavities. Important examples that can be cited include the length of stress fissures in power-driven digging apparatuses or the extent of corrosive sites in head exchange tubes of atomic power stations.

In addition to the measurement function, increasing numbers of modular-constructed expandable endoscopy systems are required. This modular capability makes possible favorable basic systems which can be retrofitted to form measurement systems when necessary. This retrofitting can also be specific to the particular application, with corresponding special accessories. In practice such retrofitting to form measurement systems occurs through corresponding replaceable heads and the related computer software. In addition, the system availability also increases thanks to the modular structure, because defective parts (replaceable heads) can be exchanged.

U.S. Pat. No. 6,184,923 B1 introduces an endoscope of the aforementioned type with replaceable heads. In one embodiment the head receives, in addition to illumination lenses, two separated lenses which form images on a common image sensor in the insertion part. With the help of the stereoscopic imaging, measurements can also be made on the observed object.

The illumination and imaging device can be conducted in the head by direct extension of the insertion part or can be selected through appropriate diversionary means to be perpendicular to the longitudinal axis of the insertion part.

DE 35 16 164 C2 reports an endoscope with eyepiece observation, which can be outfitted with replaceable heads as an adapter for longitudinal measurement. In one embodiment, the head contains an observation lens and two projection lenses with mutually parallel optical axes. A linear reference index is represented in the eyepiece part by means of the observation lens. Index points are projected onto the object plane as shadows by the projection lenses. The optical axes of the projection lenses are oriented in such a way that the connecting line of the projected index points is directed parallel to the reference index in the eyepiece part. With known distances between the index points and the distance of their connecting line to the reference index, linear measurements can be carried out in the visual field. From the location of the index points to one another in the visual field, the distance of the observation plane to the front end of the adapter can be ascertained. Because of the index points, projected as shadows, their recognizability in the illuminated visual field is low in contrast.

DE 103 08 383.9 reports a video measurement endoscope in which the functional units of operating part, shaft, and head part can be distinguished although these functional units are not interchangeable.

The head part contains, in addition to an illumination fiber bundle, a video reception system and a projection system for producing a measurement pattern on an object field. The projection system is supplied with laser light, for instance by a single-mode optical fiber. The optical fiber is conducted into the head part by the operating part. The light emission surface lies in the focal point of a collimation lens for producing a collimated sample beam bundle. A number of collimated sample beam bundles, precipitating in several directions and formed by a projection eyepiece as illuminating points on the object field, are formed out of the sample beam bundles by means of a diffractive eyepiece.

The advantage of this use of a diffractive eyepiece consists in the fact that it also allows the production of fine-structure projection patterns for increasing the measurement exactitude. The use of laser light yields a very good recognizability of the projection pattern. Because of the collimation of the sample beam bundles, the projection patterns can be depicted over a large distance to the object field.

A first possibility of severing the shaft and head parts could consist in the fact that the single mode fiber and the illumination fibers are infused at the point of division and then polished off for light transfer that is low in losses. This severing method requires a minimum shaft cross-section but instead demands that the core areas of the single mode fibers must coincide on one another upon being joined, with a precision of approximately 0.3 cm. If the gap is greater, then little or no more light passes through the single-mode fibers. Such a precision requires an excessive construction cost that can scarcely be achieved, especially if it is desired to combine all possible shafts with all possible severed head parts.

A second possible of severing consists, in turn, in a cast and polished-off shaft end. The illuminating light is taken up in the severed head part, for instance by fibers or glass bodies. In addition the head part contains a collimation lens for receiving the measurement light. On coupling on the head part, the end of the infused single-mode fibers on the shaft end comes to rest in the focal point of the collimation lens, whose emerging beam bundle defines the direction of the projection pattern.

It becomes clear from the foregoing considerations that the installation of the two severed parts to one another likewise ought to occur free of any free play for sliding, which requires a considerable construction cost. Sliding of the head part through forces, impacts, or on exchange would result here in angled displacements of the projection pattern, so that measurement errors would occur. In the manufacture of individual head parts the mutual position of the fiber exiting and insertion surfaces, predetermined by the shaft, ought likewise to be maintained very precisely. Because of the likelihood of these technical difficulties, it was not possible to achieve replaceability of the head on the known system.

It is the object of the invention to make it possible to mount replaceable head parts for a video measurement endoscope, so that both individual measurement points and several measurement points in parallel projection as well as multi-point patterns can be depicted simply and with high recognizability and so that the demands on the positioning exactitude of the head part with respect to the shaft part allow high tolerances.

SUMMARY OF THE INVENTION

This object is fulfilled with an endoscopic video measurement system of the aforementioned type in such a manner that in the insertion part for transmitting a measurement ray, a single-mode optical fiber is provided, with which an optical system is associated that is positioned in the distal end part of the insertion part for creating a collimated sample beam bundle. Advantageous refinements can be seen from the characteristics of the subsidiary claims.

The collimated sample beam bundle, now transmitted into the replaceable head as a consequence of the inventive displacement of the collimation of the sample beam bundle into the insertion part, can also be directed onto the object field without further optical imaging means. Because the measurement point diameter over the entire working area is meant to be as small as possible, the sample beam bundle can also be produced with a collimation lens of small diameter. The additional necessary cross-section required for creating the collimated sample beam bundle on the distal end of the insertion part can be kept small in this manner.

In the installation of the replaceable heads it is important that the directions of the projection beam bundles are independent of the free play of the locking mechanism and of production tolerances. In this manner, tilting errors can be prevented by the relatively large plane mounting surfaces. Lateral displacement errors, however, cannot be ruled out. However, within the collimated sample beam bundle, they have no influence on the direction and the cross-section of the sample beam bundle, because the free diameter of the lens in the replaceable head is sufficiently larger than the diameter of the sample beam bundle. In addition, longitudinal displacements owing to subsequent optical divergence and dividing means in the replaceable head are non-critical in the system for the maintenance of the direction of the optical axis, which allows greater degrees of freedom for the arrangement of optical diffractive and projection means in the replaceable head.

Because of the inventive concept of the collimated parallel light passage through the interface between distal end part of the insertion part and the replaceable head, a mounted replaceable head is not required to be positioned with lateral precision to the $1/100^{th}$ of a millimeter. What is important is that the rotation and diffraction to the optical axis coincide, that is, that the replaceable head must be positioned level and the rotation position, for instance through juxtaposed bayonet capsules, is defined to allow no free play.

Embodiments of the measurement system are schematically depicted in the illustrations and are explained in greater detail with reference to these illustrations.

BRIEF DESCRIPTION OF THE DRAWINGS

FIG. 4a/b shows a view and a longitudinal sectional view on the exit end of the insertion part.

FIG. 5a/b shows a cross-sectional view through a replaceable head in 00 feed-through and with 900 deflection for a single-beam measurement system.

FIG. 6a/b shows a cross-sectional view through a replaceable head in 00 feed-through and with 900 deflection for a parallel beam measurement system.

FIG. 7a/b shows a cross-section view through a replaceable head in 00 feed-through and with 900 deflection for a multi-point measurement system.

DETAILED DESCRIPTION OF THE INVENTION

Figures 1, 2, 3:
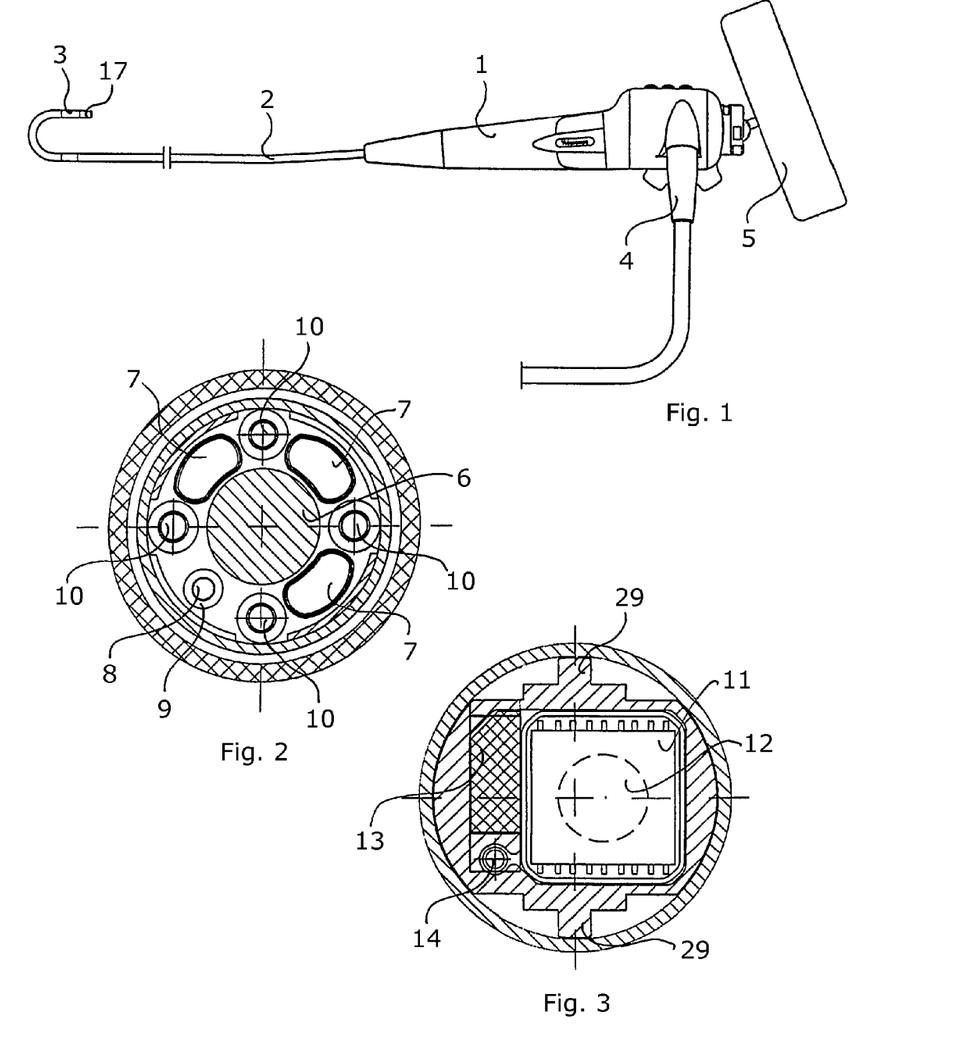
FIG. 1 shows a frontal view of the probe of an endoscopic video measurement system.
FIG. 2 shows a cross-sectional view through the insertion part in the middle area.
FIG. 3 shows a cross-sectional view through the distal end area of the insertion part.

The probe of an endoscopic video measurement system illustrated in FIG. 1 consists of an operating part 1, an insertion part 2, a distal end part 3, and a replaceable head 17. In addition to the probe, the complete measurement system consists also of a multi-function console device for light source (not illustrated), video camera controlling unit, keyboard, main monitor, and computer for image processing, measurement function, and laser control, power supply, and so on.

Provided on the operating part 1 is a connection 4 for electrical and optical supply of the measurement system. The image representation occurs by way of a video monitor 5. The illuminating can be regulated and the viewing direction of the head part 3 can be modified, for instance by additional buttons and gears available on the operating part 1 but not described in greater detail.

The cross-section through the insertion part 2 depicted in FIG. 2 shows, schematically in the center, an electrical control bundle 6. Around it are positioned, for instance, three light fiber bundles 7 and a single-mode optical fiber 8 with protective sleeve 9. The viewing direction of the distal end part 3 can be changed to a flexible distal end area of the insertion part 2 by means of four mutually symmetrically positioned Bowden cable In the cross-section on the distal end part 3 of the insertion part 2 illustrated in FIG. 3, a CCD image sensor 11 and an upstream imaging lens 12 and bayonet capsule 29 can be seen. In addition, a prism 13 is positioned, which on the rear side is coupled with the light fiber bundles 7 and by which the object illumination takes place. Below the prism 13 a collimation lens 13 is mounted for producing a collimated sample beam bundle 15. The optical imaging and diversion means for transforming the sample beam bundle are contained in the replaceable head 17, which is not described further here.

Figure 4:
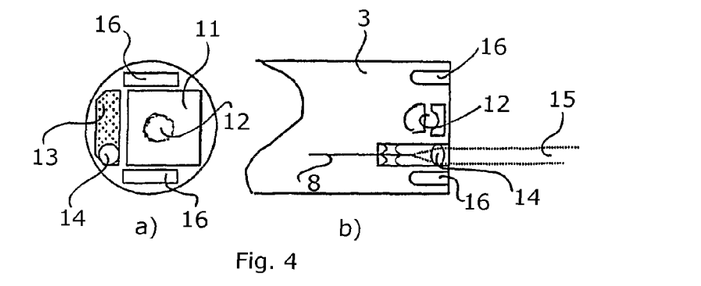

FIG. 4a shows a view of the distal end part 3 of the insertion part 2 according to the invention, where the parts already described with reference to FIG. 3 retain the same numbering. An optical system 14 for producing a collimated sample beam bundle 14 is associated with the single-mode optical fiber 8, as can be seen from FIG. 4b. The collimation system here can contain a gradient lens (GRIN) and/or an aspherical lens with minimal spherical aberration. In the distal end part 3 of the insertion part 2, recesses 16 are positioned, which correspond to the exactly positioned mounting of replaceable heads having alignment pins mounted on them.

With the sample beam bundle 15 emerging collimated from the distal end part 3, the endoscopic video system already forms a functionally capable single-beam measurement system, but with less image quality. The distance to the object can be unequivocally determined by the parallax motion of the light point in the image of the object field. As a result, the imaging scale can be defined in a level object surface oriented at a right angle to the viewing direction. A longitudinal determination in the image can be performed with the ascertained imaging scale.

Figure 5:
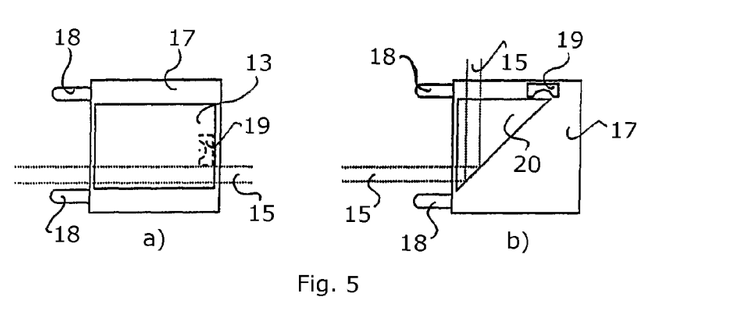

By applying a replaceable head 17 illustrated in FIG. 5a with alignment pins 18, a single-beam measurement system can be produced in turn in a 00 feed-through of the sample beam bundle 15, but with decidedly better image quality. The alignment pins 18 correspond with the recesses 16 in the end surface of the insertion part 2 and ensure the reciprocal orientation between the distal end part and the replaceable head 17.

The imaging lens for selecting the field of sight is schematically presented as distal inlet lens 9. For the sake of simplicity, possible subsequent lenses and prisms are omitted here and in the following embodiments. The control of the illumination light is to take place in the rectangular-solid-shaped prism 13. In the embodiment according to FIG. 5b, the illumination light is deflected by 900 by means of the 900 prism 20. In both embodiments the sample beam bundle 15 is likewise conducted through the prisms 13, 20.

Figure 6:
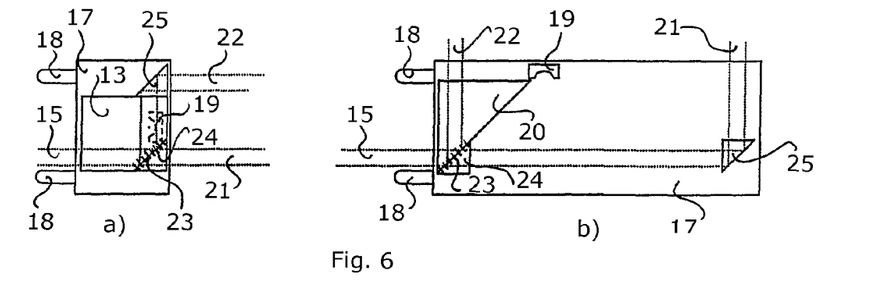

FIG. 6 shows a variant of the replaceable head 17, in which two sample beam bundles 21, 22 are formed parallel to one another from the sample beam bundle 15. In the 00 feed-through according to FIG. 5a, the rectangular-solid-shaped prism 13 on the distal side contains a facet 23, which stands at 450 to the beam direction, and on which a first 900-deflection prism 24 is cemented. The cement surface contains, for instance, a metallic reflecting element, which directs 50 percent of the laser light below 900 to the sample beam direction to an additional 900-deflection prism 25, which is cemented onto the rectangular-solid-shaped prism 13 without reflecting element in the cement surface and which reflects additional sample beam bundles 22 on its base surface parallel to the first sample beam bundle 21. The latter bundle passes through the metallically reflecting tapering 2 and the first deflection prism 24.

In a metallic reflecting cement, the severing ratio is independent of the polarization direction of the emerging laser beam. As single-mode optical fiber, a non-polarization-containing fiber is used here.

In using a polarization-continuing single-mode glass fiber, a dielectric, polarizing severing layer can be provided. The single-mode optical fiber here should be secured in the distal end part 3 in such a way that when the replaceable head 17 is mounted, the polarization direction of the severing layer stands below 450 to the polarization direction of the transmitted sample beam bundle. The use of polarized sample beam bundles that are perpendicular to one another produces particular effects in interaction with certain object surfaces.

In the 900 version according to FIG. 6b, a corresponding first 900 deflection prism 24 is cemented onto the 900 prism 20, so that the cementing surface in turn is reflected with 50% permeability, so that in transmission the first sample beam bundle 21 and in reflection the additional sample beam bundle 22 emerge. The first sample beam bundle 21 passing through the first deflection prism 24 is emitted parallel to the other sample beam bundle 22 by an additional 900 deflection 25. It is important to be alert to a corresponding orientation of the deflection prism 25 during installation. The measurement basis of the parallel beam measurement system can be influenced in simple manner by the distance of the other deflection prism 25 to the first deflection prism 24. An enlarged measurement basis increases the measuring exactitude, in particular with larger working distances.

Figure 7:
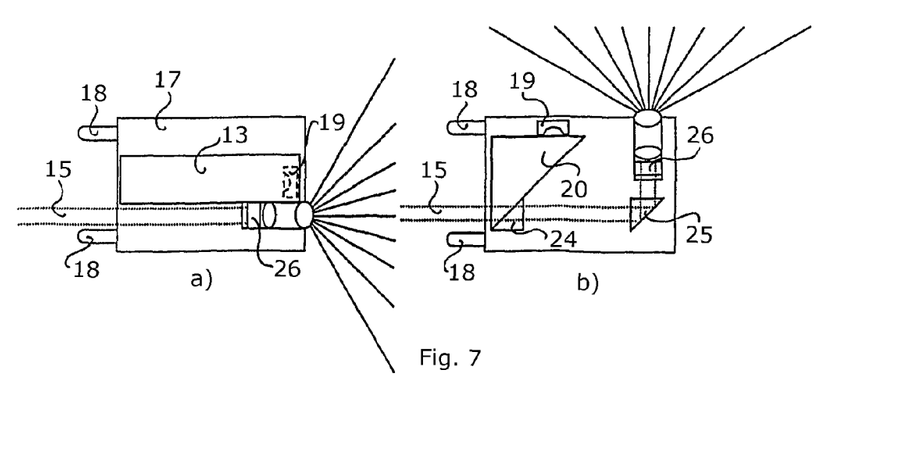

The embodiment of a replaceable head 17 illustrated in FIG. 7 shows the use of a diffractive optical element 26 (DOE) for a beam multiplication into several diverging collimated beam bundles. The way such a multi-point measuring system operates is known. A use of the point pattern is possible by exchange the DOE 26. A 00 feed-through according to FIG. 7a or a 900 deflection according to FIG. 7b is possible with the same means as shown and described in FIG. 6.

Figure 8:
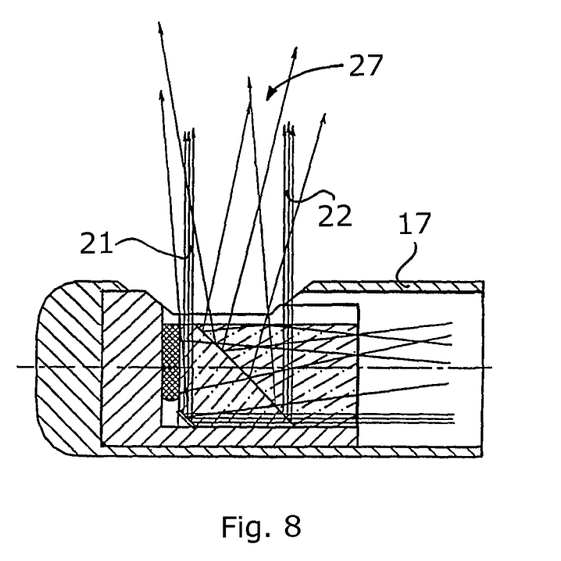
FIG. 8 shows a longitudinal sectional view through a replaceable head for 900 deflection in the area of the connecting prism for illumination and sample beam.

The embodiment illustrated in FIG. 8 shows a longitudinal section through a replaceable head 17 in the 900 deflection version in the area of the illumination beams 27 and the sample beam bundles 21, 22. The deflection and transmission means described in FIG. 6b are combined here in a compact composite prism.

Figure 9:
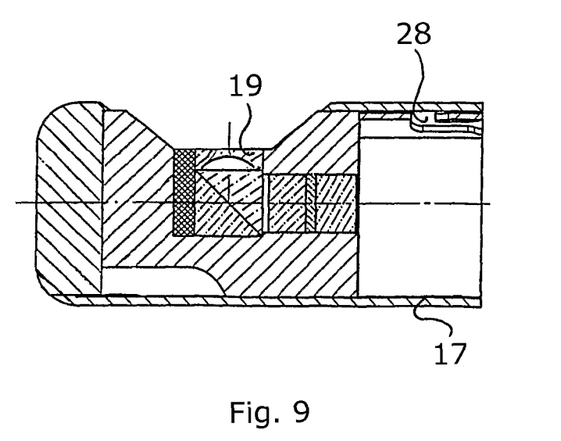
FIG. 9 shows a longitudinal sectional view through a replaceable head for 900 deflection in the area of the imaging means.

The longitudinal section illustrated in FIG. 9 on the same replaceable head 17 contains the distal inlet line 19 and deflection means for transmitting the imaging rays. The replaceable head 17 is pushed onto the distal end part 3 of the insertion part and is oriented and fixed in place, for instance by a bayonet bolt 28. The associated bayonet capsules 29 are not depicted here (compare FIG. 3).

The theoretical illustrations shown in FIGS. 4 to 7 clarify the number of configuration possibilities for the replaceable heads, which are obtained only because the sample beam bundle emitted on the distal side from the insertion part is collimated. Additional projection theories, which transform the collimated laser beams in the replaceable head into a projection patter, can be, for instance, the following:

a) Antiparallel Beams

In a parallel-beam measurement system, both beam bundles can be oriented antiparallel or intersecting one another, for instance to serve as index for a predetermined working distance. A predetermined working distance and thus a certain imaging standard is achieved if the two points coincide to form a single point.

b) Projection of Linear Targets with Reflection, Transmission, and Aberration Effects If the collimated, descending beam bundles in the replaceable head are focused with a lens, then in the focus there arises a point-shaped light source with physically determined extension in the area of only 1 to 3 wavelengths. If a wire or a transparent fiber is positioned on the distal side of the focus, then depending on the choice of the diameter and distances, a shadow pattern with overlaid aberration and interference appearances can be produced. The pattern consists of a dark shadow zone, whose two boundaries have an over-brightened light seam because of aberration effects. Thus there occurs an essentially stronger contrast in the image than with known shadow projections. Because of the stronger contrast and the over-brightened shadow borders, a more precise recognition of the position of the pattern is possible and thus also a more precise measurement. If in addition the independently switchable white illumination light is dispensed with in the measurement, then the contrast can be further heightened.

c) Projection of a Flattened Target

The collimated laser beam is focused in the replaceable head. The focus in turn illuminates at a certain distance, for instance a flattened hollow mask or a diapositive with any desired pattern, depicted for instance as a glass plate with metallic coverings. Through clever dimensioning of the structural dimensions and the distance between focus and target, it is possible here to force aberration effects, which reinforce the brightness edges in the image or even radically increase them.

d) Production of a Striped Pattern Through Interference

The collimated laser beam bundle is focused in the replaceable head with a cylindrical lens and divided by an optical component, for instance a Wollaston prism, and emitted again parallel at small lateral distances. At small distance between the two light emissions from a common source, there arise interference stripes, which yield the projection pattern. If needed the stripes' distance can be varied, for instance by changing the lateral distance of the light emissions.

e) Production of any Desired Pattern by Means of DOE

Instead of the point pattern, a DOE can produce virtually any desired pattern. Restrictions in the choice of pattern arise only if the DOE is meant to emerge at great angles. It is possible to have simple patterns such as single lines and parallel line groupings, crossed lines, and crossed parallel line groupings (grate pattern), rings, and so on. It is also possible to produce complex flattened patterns such as accidental patterns or patterns with flattened codings. Two or more DOE projectors can be used, which are positioned at various positions around the camera lens. Thus, vertical and horizontal line groupings can be emitted from separate projectors.

f) Production of Speckles

A divergent illumination can be produced in the replaceable head through a simple focusing, and such a divergent lighting leads to speckles in the image. These speckles can be part of a measurement manner that is known in its own right (electronic speckle interferometry.

The probe, consisting of an operating part 1 and an insertion part 2, of a video endoscope can also be reduced to a pure observation system if the single-mode optical fiber 8 is omitted. In its place it is possible to provide a separate vacant tube or the empty protective sleeve 9 and an insertion opening in the distal end of the insertion part 2. A single-mode optical fiber 8 with collimation lens 14 can also be inserted into the system subsequently by means of the insert opening. The empty tube, in addition, can be used as a working channel for the insertion of hooks, forceps, and the like, whose use in the object area can be observed by the video system. The modularity of the system is further expanded in this manner.

Figure 10:
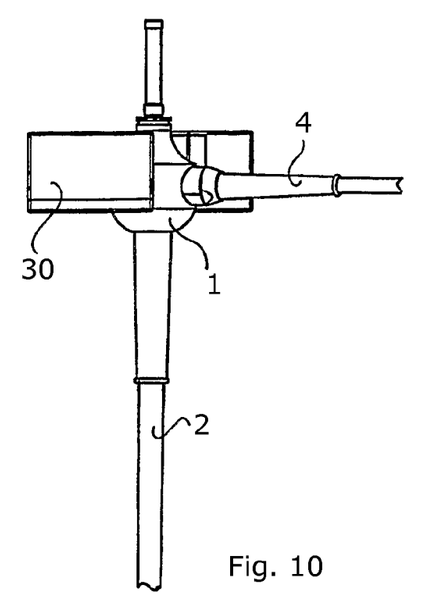
FIG. 10 shows a frontal view with an annex unit for laser light supply on the operating part.

It is advantageous here if a separate insertion aperture is provided for the feeding of the laser light into the single-mode optical fiber 8 on the operational part 1 or a plug unit connected with it, because the connection 4 for other optical and electrical supply then can remain untouched in a retrofitting into a measurement system. The laser light source in addition can be positioned in a separate housing, which can take the form of a built-on unit 30 that includes the operating part 1 or a separate plug-in unit. Such a built-on unit 30 is depicted schematically in FIG. 10 on the operating part.

As laser light source, a laser diode radiating in the visible wavelength area can be provided, in particular. Preferably the laser diode should operate at 639 nm (3 nm. For coupling the single-mode optical fiber 8 onto the laser diode, a dissoluble plug-in connection can be provided in the built-on unit 30. Repairs are facilitated by the dissoluble nature of the connection.

The laser diode employed and/or the laser diode control should be configured in such a way that speckles are reduced in the radiation field. In addition means for reducing speckles can be positioned between the laser diode and the insertion surface of the single-mode optical fiber 8. The recognizability of the measurement pattern on the object is clearly improved by suppressing speckles.

In the insertion parts 2, distal end parts 3, and replaceable heads 7 illustrated so far in the embodiments, all parts have essentially the same dimensions in cross-section. The coupling surface of the replaceable head 17 lies symmetrical to the surface of the distal end part 3.

Figure 11:
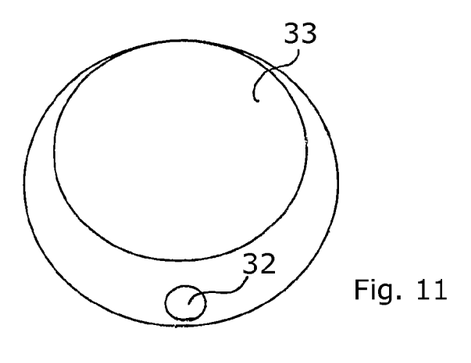
FIG. 11 shows a distal-side view of an insertion part with working channel.
Figure 11A:
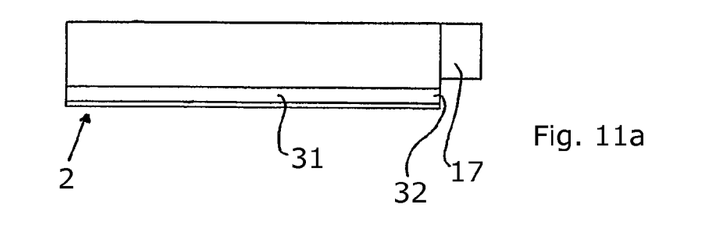
FIG. 11a shows a longitudinal sectional view through an insertion part with working channel.

As illustrated in FIGS. 11 and 11a, it is also possible, however, to provide in the peripheral area of the insertion part 2 an additional working channel 31 for inserting particular mechanical manipulation tools such as hooks and forceps. The cross-section of the insertion part 2 in the area of the distal end part 3 should then be selected to be large enough that the distal-side aperture 32 of the working channel 311 is uncovered beside the replaceable head 17. The centering and coupling means for applying the replaceable head 17 in the coupling area 33 should be placed correspondingly asymmetrical on the distal end part 3. Instruments inserted in the working channel 31 can in this way be conducted unimpeded past the replaceable head 17 to the observed object area.

What is claimed is:

1. An endoscopic video measurement system comprising:
a proximal operating part, an insertion part, and an interchangeable head which can be attached thereto, wherein the proximal operating part comprises a connection for electrical and optical supply for the system,
a first optical transmitter for object illumination and electrical supply and transmission lines for an electronic image sensor, which is arranged in a distal end portion of the insertion part, are provided in the insertion part,
the interchangeable head comprises a second optical transmitter for the object illumination and object imaging,
a single-mode glass fiber in the distal end portion of the insertion part,
an opening in a distal end surface of the insertion part that transmits light out of the insertion part,
an entrance surface of the interchangeable head that receives light from the opening when the interchangeable head is attached to the insertion part, and
an optical system associated with the single-mode glass fiber in the distal end portion of the insertion part that produces a collimated measurement beam bundle by collimating the light transmitted out of the insertion part to increase positioning tolerances between the insertion part and the interchangeable head.

2. The endoscopic video measurement system according to claim 1, characterized in that the collimated measurement bundle has associated with it an interchangeable head with an optical splitter element and at least one 90° deflection prism for producing a first and a second collimated measurement beam bundle, which beam bundle exits from the interchangeable head in a mutually parallel manner.

3. The endoscopic video measurement system according to claim 1, characterized in that the collimated measurement bundle has associated with it an interchangeable head with a diffractive optical element for producing a multi-beam bundle which exits from the interchangeable head and forms a measurement point pattern.

4. The endoscopic video measurement system according to claim 1, characterized in that a laser light source which is arranged is a separate housing is provided for supplying the single-mode optical fiber, wherein the housing is in the form of an add-on unit encompassing the operating part.

5. The endoscopic video measurement system according to claim 1, characterized in that a working channel, which is suitable for guiding mechanical manipulation means through it and whose distal-end opening lies outside the coupling region of the interchangeable head at the distal end portion, is provided in the peripheral edge region of the insertion part.

6. The endoscopic video measurement system according to claim 1, characterized in that the distal end surface of the insertion part includes a recess, and the entrance surface of the interchangeable head includes an alignment pin opposite of and engageable in the recess.

7. The endoscopic video measurement system according to claim 1, characterized in that the distal end surface of the insertion part includes at least two recesses, and the entrance surface of the interchangeable head includes at least two alignment pins, each of the alignment pins being opposite of and engageable in one of the recesses.

\* \* \* \* \*